United States Patent [19]
Sarvazyan et al.

[11] Patent Number: 5,265,612
[45] Date of Patent: Nov. 30, 1993

[54] INTRACAVITY ULTRASONIC DEVICE FOR ELASTICITY IMAGING

[75] Inventors: Armen P. Sarvazyan, Pushchino, U.S.S.R.; Stanislav Emelianov, Toledo, Ohio; Andrei R. Skovoroda, Pushchino, U.S.S.R.

[73] Assignee: Medical Biophysics International, Eden Prairie, Minn.

[21] Appl. No.: 994,105

[22] Filed: Dec. 21, 1992

[51] Int. Cl.$^5$ .............................................. A61B 8/12
[52] U.S. Cl. ........................... 128/660.01; 128/662.06
[58] Field of Search .................... 128/660.01, 660.07, 128/660.06, 660.02, 662.06, 661.03

[56] References Cited

U.S. PATENT DOCUMENTS

| | | | |
|---|---|---|---|
| 4,004,457 | 1/1977 | Eide et al. | 73/94 |
| 4,140,008 | 2/1979 | Golembeck et al. | 73/78 |
| 4,144,877 | 3/1979 | Frei et al. | 128/2 S |
| 4,250,894 | 2/1981 | Frei et al. | 128/774 |
| 4,802,487 | 2/1989 | Martin et al. | 128/662.06 |
| 4,819,649 | 4/1989 | Rogers et al. | 128/660.02 |
| 4,860,761 | 8/1989 | Yamasawa et al. | 128/686 |
| 4,865,041 | 9/1989 | Hassler et al. | 128/660.03 |
| 4,869,261 | 9/1989 | Penáz | 128/667 |
| 4,911,173 | 3/1990 | Terwilliger | 128/662.06 |
| 4,947,851 | 8/1990 | Sarvazyan et al. | 128/660.02 |
| 5,024,234 | 6/1991 | Leary et al. | 128/663.01 |
| 5,031,626 | 7/1991 | Hassler et al. | 128/660.03 |
| 5,080,101 | 1/1992 | Dory | 128/660.03 |
| 5,099,848 | 3/1992 | Parker et al. | 128/661.07 |
| 5,107,837 | 4/1992 | Ophir et al. | 128/660.01 |
| 5,115,808 | 5/1992 | Popovic et al. | 128/660.02 |
| 5,143,070 | 9/1992 | Ophir et al. | 128/660.01 |
| 5,178,147 | 1/1993 | Ophir et al. | 128/660.01 |

OTHER PUBLICATIONS

R. M. Lerner et al., *Sono-Elasticity: Medical Elasticity Images Derived From Ultrasound Signals in Mechanically Vibrated Targets*, Acoustical Imaging, vol. 16, 317 (1988).

L. S. Wilson et al., *Ultrasonic Measurement of Small Displacements and Deformations of Tissue*, Ultrasonic Imaging 4, 71-82 (1982).

Kumasaka, Glen, *Diagnostic Considerations in Transrectal Ultrasonic Imaging of the Prostate Gland*, The Use of Transrectal Ultrasound in the Diagnosis and Management of Prostate Cancer, pp. 57-71, 1987.

Watanabe, Hiroki, *Historical Perspectives on the Use of Transrectal Sonography of the Prostate*, The Use of Transrectal Ultrasound in the Diagnosis and Management of Prostate Cancer, pp. 5-13, 1987.

Huben, Robert, *The U.S.A. Experience: Diagnosis and Follow-up of Prostate Malignancy By Transrectal Ultrasound*, The Use of Transrectal Ultrasound in the Diagnosis and Management of Prostate Cancer, pp. 153-159, 1987.

McLeary, Richard *Future Developments in Ultrasonic Imaging of the Prostate*, The Use of Transrectal Ultrasound in the Diagnosis and Management of Prostate Cancer, pp. 209-211, 1987.

(List continued on next page.)

*Primary Examiner*—William E. Kamm
*Assistant Examiner*—George Manuel
*Attorney, Agent, or Firm*—Kinney & Lange

[57] ABSTRACT

An intracavity ultrasonic device for elasticity imaging of human tissue to obtain palpation information in a quantitative form by using a probe that has an ultrasonic transducer at one end thereof, the probe having a small diameter and being capable of being inserted inside a conduit of a body. An outer elastic sheath surrounds the probe and is sealed so that it can be filled with a fluid under pressure to create a chamber surrounding the ultrasonic transducer while the sheath is on the interior of the bodily conduit to be examined. By regulating the interior pressure, the sheath can be made to expand against the interior of the conduit and change the deformation of the tissue forming the conduit. The sheath includes a region of greater elasticity adjacent the transducer to facilitate localized deformation of a selected region of the bodily conduit wall. Obtaining images of the selected conduit region before and after compression provides data to calculate the elasticity of tissue in that region and surrounding regions. Elasticity is an informative characteristic for tumor detection as is known from the palpation technique of detecting tumors.

6 Claims, 8 Drawing Sheets

OTHER PUBLICATIONS

Yamakoshi, Yoshiki et al., *Ultrasonic Imaging of Internal Vibration of Soft Tissue under Forced Vibration,* IEEE Transactions on Ultrasonics, Ferroelectrics and Frequency Control, vol. 37, No. 2, pp. 45–53, Mar. 1990.

Ophir, J. et al., *A Transaxial Compression Technique (Tact) for Localized Pulse-Echo Estimation of Sound Speed in Biological Tissues,* Ultrasonic Imaging 12, 35–46 (1990).

Ophir, J. et al., *Elastography: A Quantitative Method for Imaging the Elasticity of Biological Tissues,* Ultrasonic Imaging 13, 111–134 (1991).

Tanouchi, J. et al., *Visualization of Local Elasticity of Artery to Evaluate Arteriosclerosis with Digital Subtraction Echography (DSE) Preliminary Study,* pp. 190–191.

Ishihara, K., *High-Speed Digital Subtraction Echography: Principle and Preliminary Application to Arteriosclerosis, Arrhythmia and Blood Flow Visualization,* 1990 Ultrasonics Symposium, pp. 1473–1476.

Gentle, C. R., *Mammobarography: A Possible Method of Mass Breast Screening,* Journal Biomed. Eng. 1988, vol. 10, Apr., p. 124.

Krouskop, T. A. et al., *A Pulsed Doppler Ultrasonic System for Making Noninvasive Measurements of the Mechanical Properties of Soft Tissue,* Journal of Rehabilitation Research and Development vol. 24, No. 2, 1987, pp.1 1–8.

Martin, June, *Transrectal Ultrasound: A New Screening Tool for Prostate Cancer,* American Journal of Nursing, Feb. 1991, p. 69.

Chodak, Gerald, *Transrectal Ultrasonography: Is it Ready for Routine Use?,* Jama, May 13, 1988, vol. 259, No. 18, pp.2744–2745.

*Diagnostic and Therpeutic Technology Assessment (DATTA),* Jama, May 13, 1988, vol. 259, No. 16, pp. 2757–2758.

Pipe, James et al., *Method for Measuring Three-Dimensional Motion with Tagged MR Imaging,* Radiology 1991; 181:591–595.

Lerner, Robert et al., *"Sonoelasticity" Images Derived From Ultrasound Signals in Mechanically Vibrated Tissues,* Ultrasound in Med. & Biol., vol. 16, No. 3, 1990, pp. 231–239.

Parker, K. J. et al., *Tissue Response to Mechanical Vibrations for "Sonoelasticity Imaging",* Ultrasound in Med & Biol., vol. 16, No 3, 1990, pp. 241–246.

Yamashita et al., *Tissue Characterization from Ultrasonic Imaging of Movement and Deformation,* 1990 Ultrasonics Symposium, pp. 1371–1375.

Publication: *Acoustic Images,* Issue 4, Summer 1991.

Publication: *Acoustic Images,* Issue 5, Winter 1991.

Tristam et al., *Application of Fourier Analysis to Clinical Study of Patterns of Tissue Movement,* Ultrasound in Med. & Biol. vol. 14, No. 8, pp. 695–707, 1988.

Tristam et al., *Ultrasonic Study of In Vivo Kinetic Characteristics of Human Tissues,* Ultrasound in Med. & Biol. vol. 12, No. 12, pp. 927–937, 1986.

Dickinson et al., *Measurement of Soft Tissue Motion Using Correlation Between A-Scans,* Ultrasound in Med & Biol. vol. 8, p. 263, 1982.

*Diagnostic and Therpeutic Technology Assessment (DATTA),* Jama, Mar. 16, 1990, vol. 263, No. 11, pp. 1563–1568.

INTRACAVITY ULTRASONIC DEVICE FOR ELASTICITY IMAGING

BACKGROUND OF THE INVENTION

The present invention relates to an intracavity probe assembly insertable into a bodily conduit such as an endorectal or endovaginal probe. An ultrasonic transducer is carried with the probe assembly and used for obtaining an ultrasonic image of a cross section of the conduit under deformation and no deformation (relaxed) conditions.

Intrarectal and intravaginal palpation is widely used in examination of patients to detect prostate tumors and other cancers by evaluating the hardness of the palpated area of the rectum or vagina. This palpation is commonly performed using a finger of the physician and as such involves much subjectivity in determining the presence of tumors.

At the present time, intracavity probes for ultrasonic imaging are known having ultrasonic transducers capable of being inserted into bodily conduits, such as the esophagus, rectum, and vagina. These endoscopic probes are used for obtaining ultrasonic images of surrounding tissue under static conditions. The available probes provide up to 360° scanning. The usefulness of such probes extends only to direct imaging and the information provided by those ultrasonic devices does not contain the evaluation of relative hardness of tissues, which can be reconstructed from the comparison of images when wall tissue is deformed at one time and relaxed at another.

Acoustic Imaging of Phoenix, Arizona sells a slightly curved endorectal ultrasonic probe with a field of scan or view that provides both transverse and sagittal scanning images of the prostate without application of forces compressing tissue.

Techniques used for intrarectal ultrasound have been discussed in literature and various approaches have been tried. See for example, Martin, J. P. Transrectal ultrasound: A New Screening Tool for Prostate Cancer", American Journal of Nursing; Page 69; February 1991. The following items in the Journal of the American Medical Association have dealt with the techniques where use of a condom on an ultrasonic probe is mentioned: Chodak, G. W.; Transrectal Ultrasonography: Is It Ready for Routine Use?; JAMA 259:18 Pages 2744-2745; May 13, 1988 and Questions and Answers: JAMA 259:18, Pages 2757-2759; May 13, 1988.

A method recently proposed for measuring and imaging tissue elasticity is described in Ophir et al., U.S. Pat. No. 5,107,837. This method includes emitting ultrasonic waves along a path into the tissue and detecting an echo sequence resulting from the ultrasonic wave pulse. The tissue is then compressed (or alternatively uncompressed from a compressed state) along the path by displacing a transducer and during such second compressing, a second pulse of ultrasonic waves is sent along the path into the tissue. The second echo sequence resulting from the second ultrasonic wave pulse is detected and then the differential displacement of selected echo segments of the first and second echo sequences are measured. A selected echo segment of the echo sequence, i.e., reflected RF signal, corresponds to a particular echo source within the tissue along the beam axis of the transducer. Time shifts in the echo segment are examined to measure compressibilities of the tissue regions. This technique is further described in Ophir et al., *Elastography: A Quantitative Method for Imaging the Elasticity of Biological Tissues*. Ultrasonic Imaging 13, 111 (1991).

Despite the advent of intrarectal probes for ultrasonic imaging of bodily conduit tissues, the procedure of palpating bodily conduits with a finger is still widely used. This procedure is highly subjective and does not provide complete information about the presence, location, size, and relative hardness of an inclusion (e.g. tumor). This is especially true when the tumor is small and/or far from the bodily conduit wall.

SUMMARY OF THE INVENTION

The present invention allows a physician to objectively and quantitatively obtain palpatory information without using the common subjective procedure of palpating by inserting a finger into the bodily conduit (e.g. rectum). The present invention allows one to obtain complete palpatory information including the presence, location, size, and relative hardness of a lesion, such as a cyst or a tumor, adjacent a bodily conduit such as a rectum. Moreover, the probe of the present invention permits detection and palpatory information gathering of tumors deep within tissue relative to the bodily conduit (i.e. tumors not close to the bodily conduit wall) in cases in which conventional finger palpation techniques could not even detect the presence of the tumor.

The present invention includes an ultrasonic probe which is adapted to be inserted into a bodily conduit for deforming the conduit wall and adjacent tissue while an ultrasonic imaging device is operating. The pressure on the wall of the bodily conduit is selectively varied so that tissue may be imaged under different deformation conditions.

The device as shown includes a rubber sheath that surrounds a probe which contains an ultrasonic transducer adjacent the inserted end of a probe. The sheath is condom-like and is closed at a leading or inserted end and sealed to the exterior of the probe at its opposite or remote end. The sheath is capable of being filled with water or other sonic energy coupling medium.

The sheath is capable of being pressurized at different selected pressures through a suitable conduit at the same time that the ultrasonic transducer in the probe (on the interior of the sheath) is providing an ultrasonic image. The sheath size and shape can be controlled to create desired pressure on the wall resulting in changes in deformation of wall tissue and adjacent tissue. In particular, the sheath shape is adapted to create a desired pressure on a selected portion of the wall of the bodily conduit resulting in changes of deformation in the localized area of the selected wall portion of the bodily conduit and adjacent tissue. Changes in pressure on the walls of the bodily conduit are achieved by varying the pressure in the sheath to expand the bodily conduit wall and then permit the wall to contract. An ultrasonic image of the tissue being examined is obtained before deformation by the sheath and after the deformation (i.e., while the tissue is under the desired level of compression) of another ultrasonic image is obtained. Analyzing the difference in the images reflects the elasticity of the wall tissue and the elasticity of a tumor within adjacent tissue.

The outer sheath contains a liquid that is a coupling medium for the ultrasonic energy of the ultrasonic transducer to aid in obtaining ultrasonic images. Water has been found to be a suitable coupling medium.

Various forms of attachment to move the transducer and sheath longitudinally can be made in a known manner. The ultrasonic imaging probe is preferably in the tip of an elongated rod-like slender body so that it can be inserted into a bodily conduit at a desired location and the sheath can be expanded when the location of examination is reached. A series of longitudinally spaced images of cross sections of the bodily conduit can be made before and under selected pressure conditions to determine the conditions of the adjacent tissue under elastic deformation. This series of images can be used for three dimensional reconstruction of visible structures so that by analyzing the deformation of three dimensional structures, elastic moduli can be evaluated.

DETAILED DESCRIPTION OF THE PREFERRED EMBODIMENTS

Co-pending U.S. patent application Ser. No. 7/994,109, filed on even date herewith and owned by the same assignee as the present application, for METHOD AND APPARATUS FOR ELASTICITY IMAGING discloses that deforming bodily tissue permits one to determine variations in the elasticity of tissue in areas of the body. Moreover, through analysis one can determine whether there are abnormal changes in elasticity and therefore determine if there are tumors or other pathological tissues present, which have a different elasticity than the surrounding tissue. This principle, as explained in the co-pending application, is applied to the present device, which is an intracavity probe. By using the intracavity probe of the present invention, one can objectively and quantitatively obtain palpatory information such as the presence, location, size, and relative hardness of a tumor adjacent the wall of a bodily conduit such as the rectum or vagina. Moreover, this palpatory information can be obtained by the present invention without inserting a finger into the bodily conduit. More importantly, the present invention permits detection of tumors in cases where the subjective finger palpation would not indicate the presence of a tumor at all, such as when the tumor is quite small or deep within the tissue (not close to the bodily conduit wall).

Figure 1:
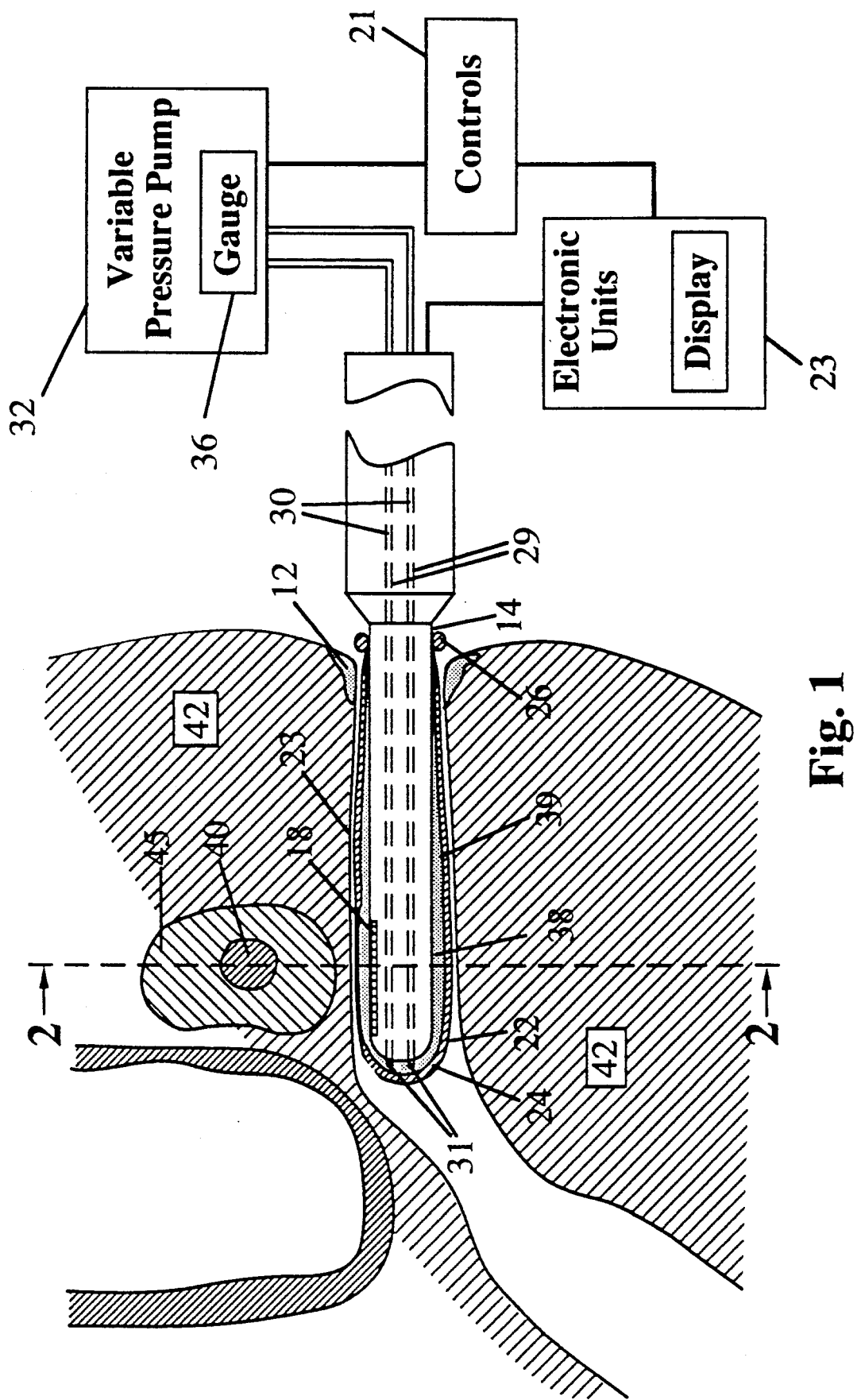
FIG. 1 is a schematic longitudinal sectional view through a portion of the lower colon showing device made according to the present invention in place therein.
Figure 2:
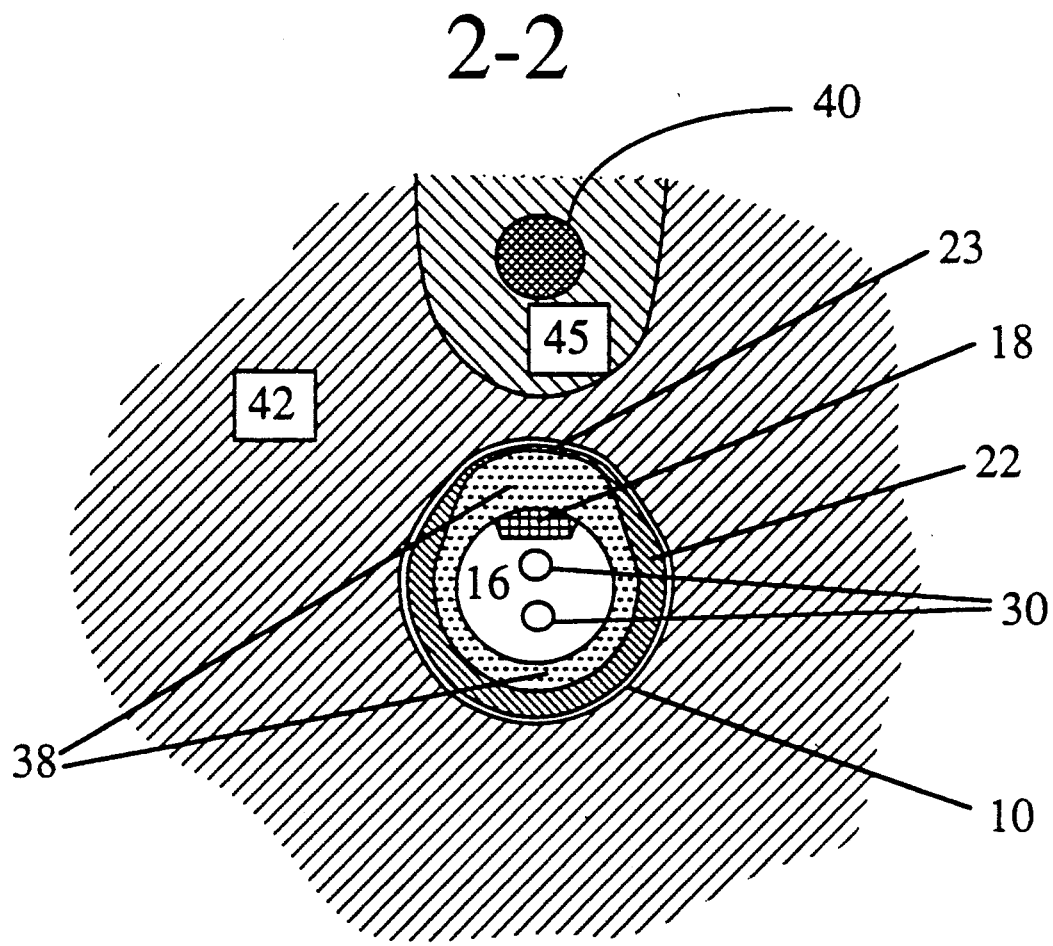
FIG. 2 is a sectional view taken as on line 2—2 in FIG. 1.

As seen in FIGS. 1 and 2, a lower colon such as that shown at 10 comprises tissue forming a bodily conduit wall. The lumen 12 of the conduit 10 may be expanded and retracted because of the conduit tissue elasticity. An intracavity probe assembly 14 is inserted into the lumen 12 of the conduit to examine the condition of the tissue of the colon conduit 10 as well as surrounding tissue.

The probe assembly 14 includes a central elongated rod-like probe 16 having sufficient rigidity for insertion and which has a smaller diameter than the lumen 12. The probe 16 can be inserted into the lumen or cavity (e.g., rectum and colon) through a bodily orifice (e.g., anus). An ultrasonic transducer array 18, which sends out ultrasonic energy and receives reflected ultrasonic energy is mounted on a inserted end of the probe 16 as is well known. Suitable leads shown at 20 are connected to the transducer 18. The leads 20 are connected to controls 21 which include electronic units 23 including computers, a display for the images, and recording devices.

The leading or inserted end portion of the probe is surrounded by an elastic or rubber sheath cylinder 22, which is similar to a condom or balloon. The sheath 22 has a closed, rounded leading end 24, as shown, and a neck portion 26 at the remote end (opposite the leading end), which seals against the surface of the probe 16 at a distance spaced rearwardly from the transducer array 18.

The sheath 22 has a wall that is elastic but includes a region 23 that is thinner or more readily stretched than the major portion of the sheath 22 so that the region 23 will expand more readily and tend to bulge out. This causes increased deformation in a selected region of the wall of the colon 10 (or other bodily conduit) adjacent the expanded sheath region 23. The sheath region 23 of increased expandability is aligned with the transducer array 18 so that the selectively compressed tissue can be readily imaged.

The probe 16 has at least one or a pair of conduits 30 for carrying a suitable liquid therethrough and being sealingly fitted within and extending therethrough the probe 16. A proximal end 29 of the conduit 30 is connected to a suitable variable pressure pump 32 or other pressure source and a distal end 31 of the conduit 30 is open to an interior of the sheath 22. The pump 32 has a variable pressure output and can be controlled by controls 21 to vary the pressure on the interior of the sheath 22 as desired. The pressure can be controlled with a variable regulator. The controls 21 may be a computer control that includes a pressure feedback to cycle pressure in the sheath between programmed values.

The pump 32 is used for introducing liquid, such as water, into an internal chamber 38 of the sheath 22 and also is used for regulating internal pressure in the chamber 38. A pressure gauge 36 (schematically illustrated) in the conduit 30 measures a pressure on the interior of the sheath 22 which is visually displayed by unit 23. The pressure in the chamber 38 (interior) of sheath 22 can be changed as previously described.

An ultrasonic energy coupling fluid such as water 39 is shown in the chamber 38. Water aids in the transmission of the ultrasonic signals across the radial space of the chamber 38 from the transducer array 18. The ultrasonic transducer array 18 is mounted in any suitable manner to the distal end of the probe 16 and the orientation of the scanning angles can be varied, depending on the uses desired.

Ultrasonic imaging is used before and after the deformation of the conduit wall for determining variations in the tissue elasticity. Tissue 42 adjacent the wall of the conduit 10 may have a tumor such as that shown at 40. For example, tumor 40 could be a tumor within a tissue portion 45 such as the prostate. The presence of a tumor can then be diagnosed based on the mathematical reconstruction of the elastic properties of the tissue using ultrasonic imaging before deformation and after deformation (i.e., while the tissue is under the desired level of compression) of the tissue by pressure applied from the sheath 22, and in particular in the region 23 of the sheath.

The bodily conduit 10 expands when the pressure in the chamber 38 is increased and thus strain of the conduit wall tissue occurs. This strain of the conduit wall tissue can be monitored by ultrasonic imaging system using, for example, a known speckle tracking technique.

FIGS. 3-8 illustrate mathematical analysis which reconstruct the elastic properties of the examined tissue.

Figure 3:
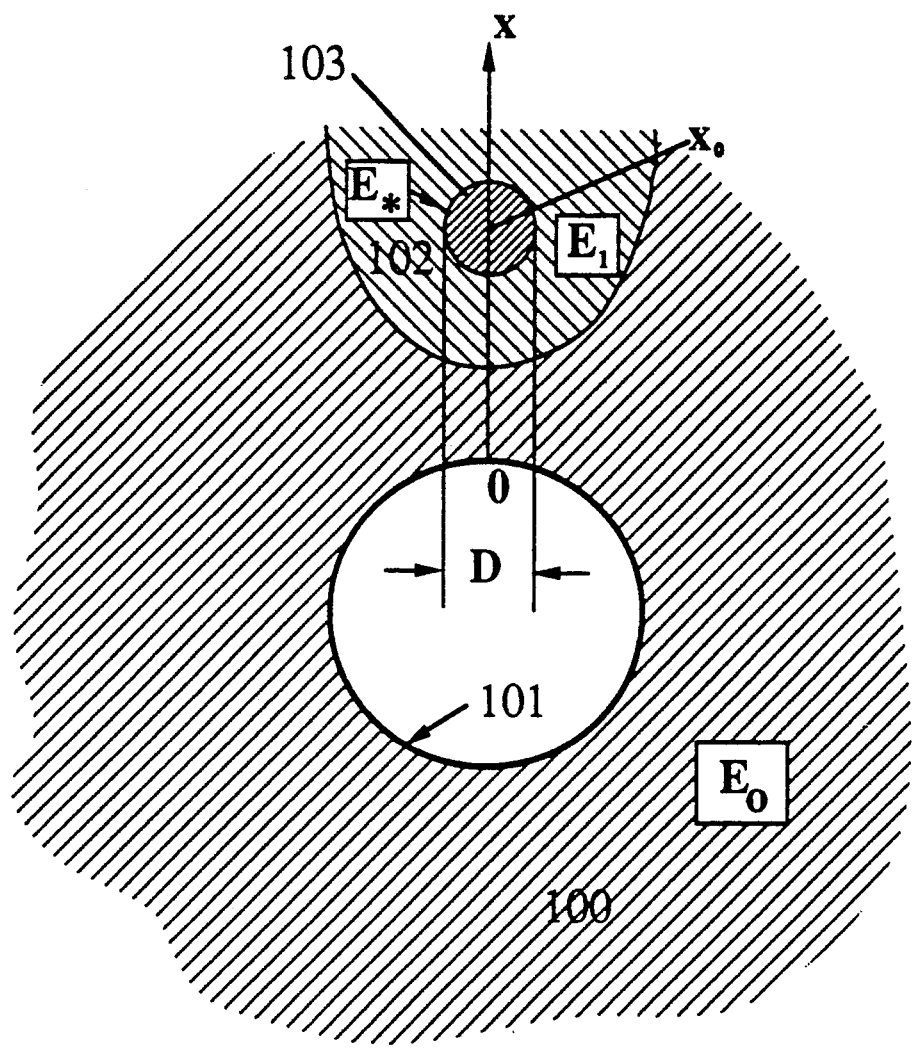
FIG. 3 is a cross-section of a schematic representation of a conduit for illustrating parameters for examining elastic properties.

In FIG. 3, a prostate 102 has a Young's modulus $E_1$ within a wall 100 of a conduit 101 having Young's modulus $E_0$. The prostate has a tumor 103 having Young's modulus $E*$ and a diameter D. The center of the tumor is in the position ($x_0$) along the x axis as shown. To illustrate the mathematical approach, the Young's moduli $E_0$ and $E_1$ were considered of the same order of magnitude. As it is presented in co-pending U.S. patent application Ser. No. 07/994,109, filed on even date herewith and owned by the same assignee as the present application, for METHOD AND APPARATUS FOR ELASTICITY IMAGING, the strain characteristic ($\epsilon = b_1/a_1$) illustrated for FIGS. 3A and 3B is sensitive to the presence of a tumor and can be successfully used for the examination of the tissue elasticity.

Figure 3A:
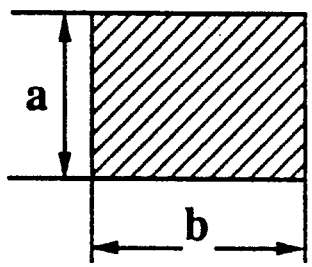
FIGS. 3A and 3B illustrate the dimensional changes in a portion of tissue before and after compression and the notation for characterizing strain in the deformed tissue.
Figure 3B:
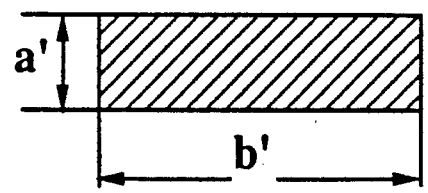

FIGS. 3A and 3B illustrate the changes in dimension of a portion of tissue when subject to a compression load. When the pressure is applied, the tissue is deformed and the initial dimensions (a) and (b) shown on FIG. 3A of any tissue portion are changed to the dimensions ($a_1$) and ($b_1$) as it is shown on FIG. 3B. The old (i.e., initial) and new sizes of the tissue portion being examined can be determined through the imaging scanner used, as shown at 18. The relation between new sizes ($b_1$) and ($a_1$) is presented as $\epsilon = b_1/a_1$ and this is called the strain characteristic.

Figure 4:
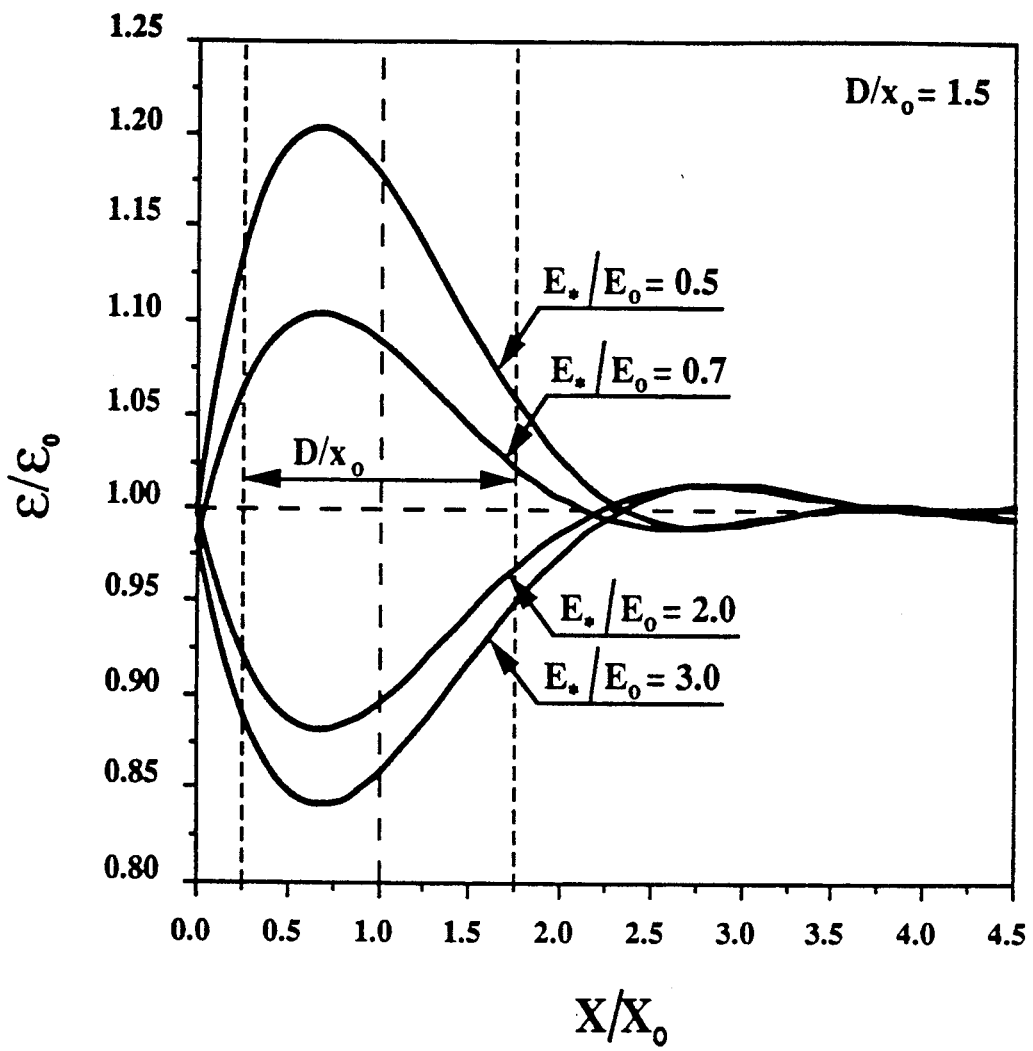
FIGS. 4 through 8 are graphical representations of strain characteristics calculated at different parameters related to FIG. 3.

FIG. 4 illustrates the calculated profiles of the relative value of the strain characteristic $\epsilon/\epsilon_0$ plotted against the x coordinate and each curve plotted is for a different value of relative Young's modulus ($E*/E_0$) (these curves are labeled in FIG. 4). The value for the dimensions shown in FIG. 3 is listed at the upper right hand corner of FIG. 4. In the case of a soft tumor ($E* < E_0$) the value of the strain characteristic $\epsilon*$ in the area inside the tumor, which is bounded by two vertical dashed lines, is larger than the value $\epsilon_0$ calculated for normal tissue, i.e., the relative value $\epsilon*/\epsilon_0 < 1$. In the case of a hard tumor ($E* > E_0$), the value of the strain characteristic $\epsilon*$ in the area inside the tumor is smaller than the value $\epsilon_0$, i.e., the relative value $\epsilon*/\epsilon_0 < 1$.

Figure 5:
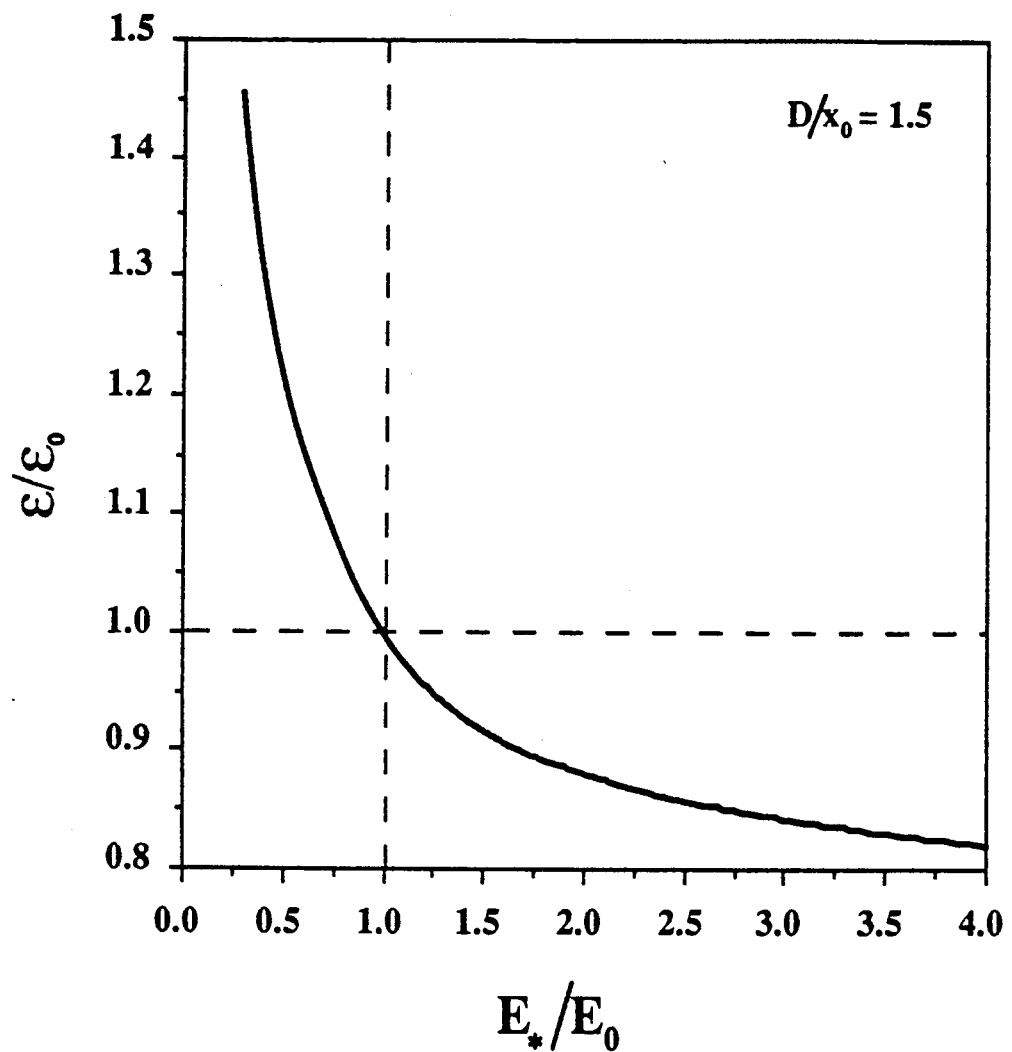

The relative value of the strain characteristic $\epsilon*/\epsilon_0$ versus the relative Young's modulus of the tumor ($E*/E_0$) is presented in the curve plotted in FIG. 5. The relative parameter for the dimensions shown in FIG. 3 is listed in the upper right hand corner of FIG. 5.

Figure 6:
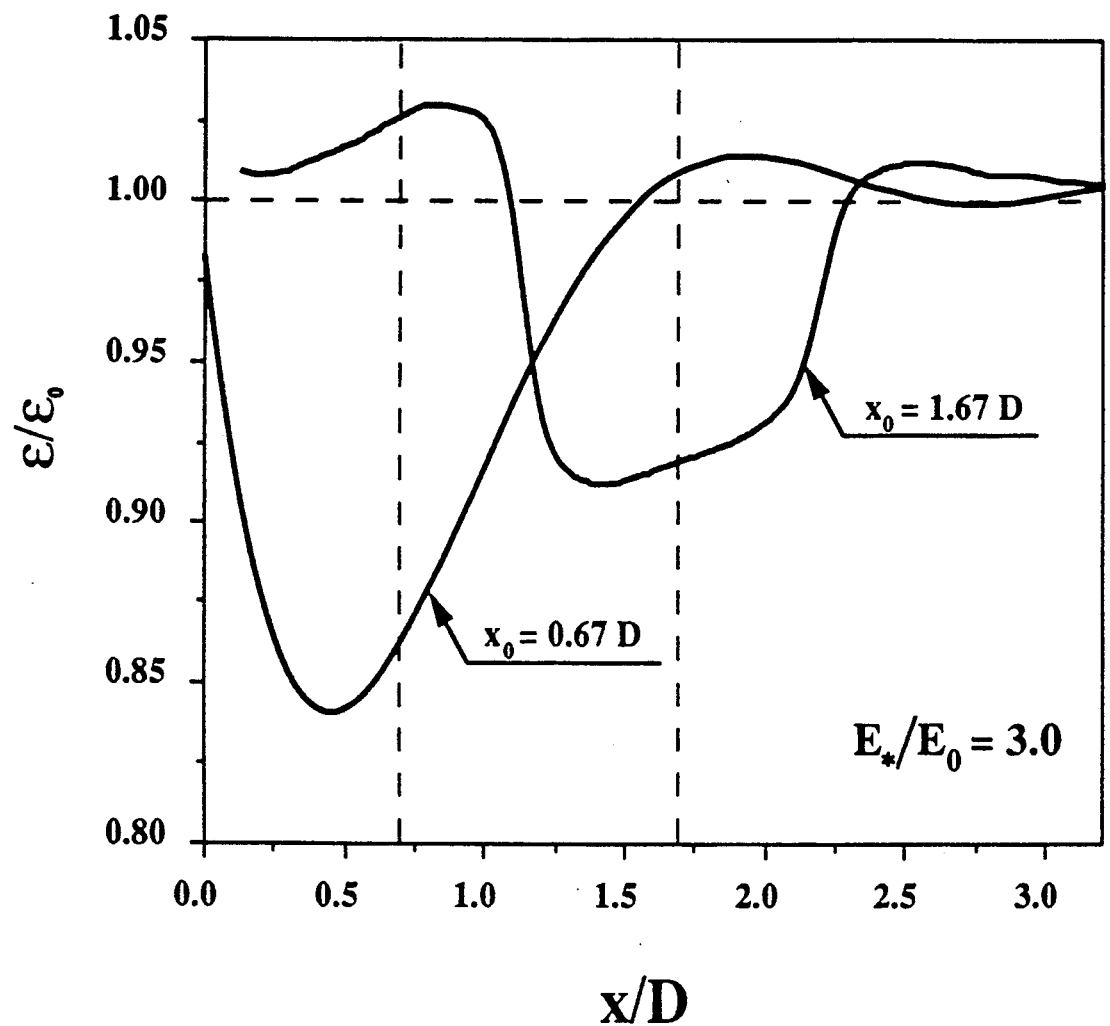

The location of a tumor can be detected by analyzing the profile of the relative strain characteristic $\epsilon/\epsilon_0$ along the horizontal x-axis, as it is shown in the curves plotted in FIG. 6 for two different locations ($x_0$) (e.g. $x_0 = 0.67D$ and $x_0 = 1.67D$) of the tumor which are represented by the vertical dashed lines. The horizontal line of the graph is x/D, the parameters X and D defined in FIG. 3. As before, the relative Young's moduli shown in FIG. 3 are listed in the lower right hand corner of FIG. 6. The Young's modulus of the tumor was assumed to be three times larger than that for surrounding tissue. The region where the relative value $\epsilon/\epsilon_0$ is a minimum are well correlated to the locations of the tumor.

Figure 7:
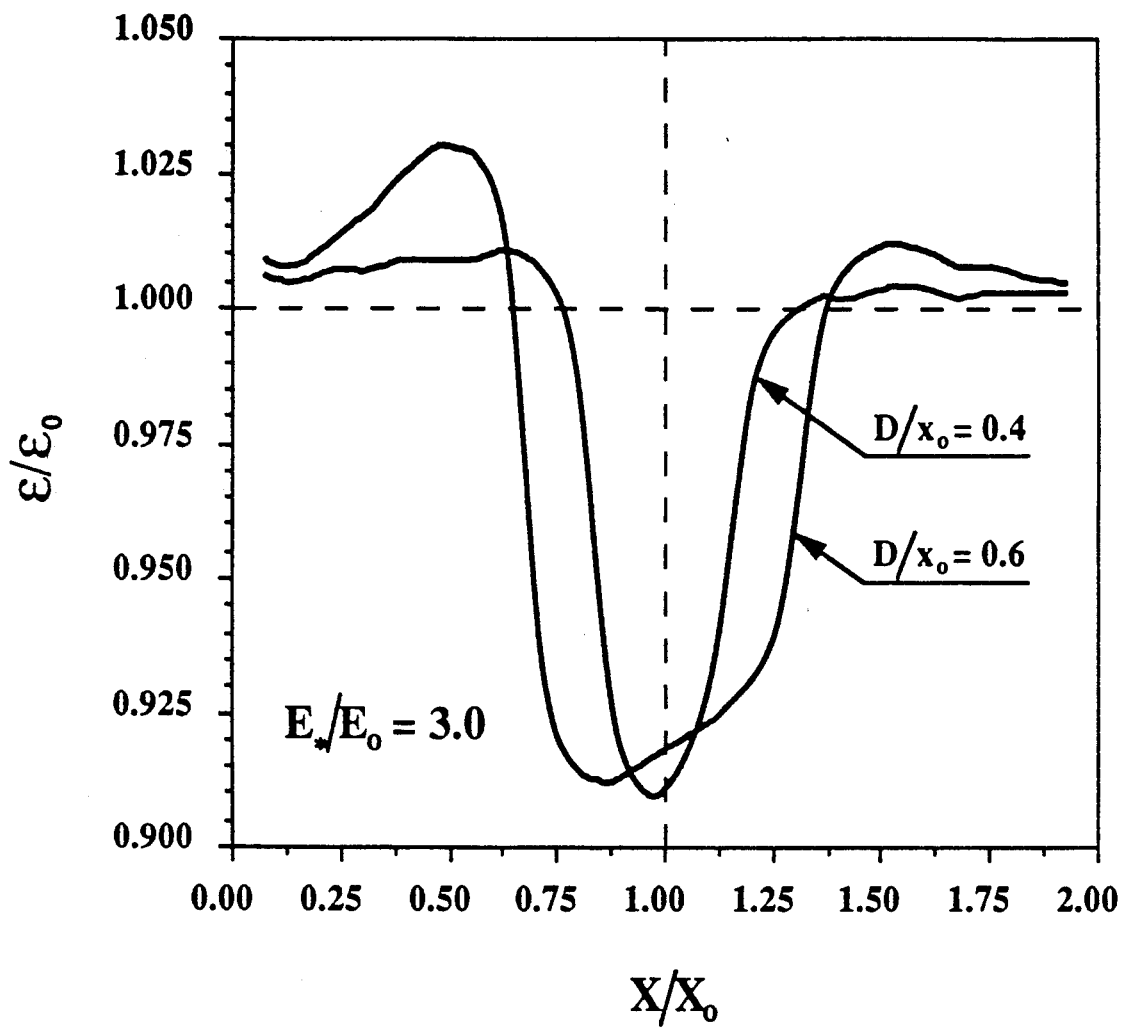
Figure 8:
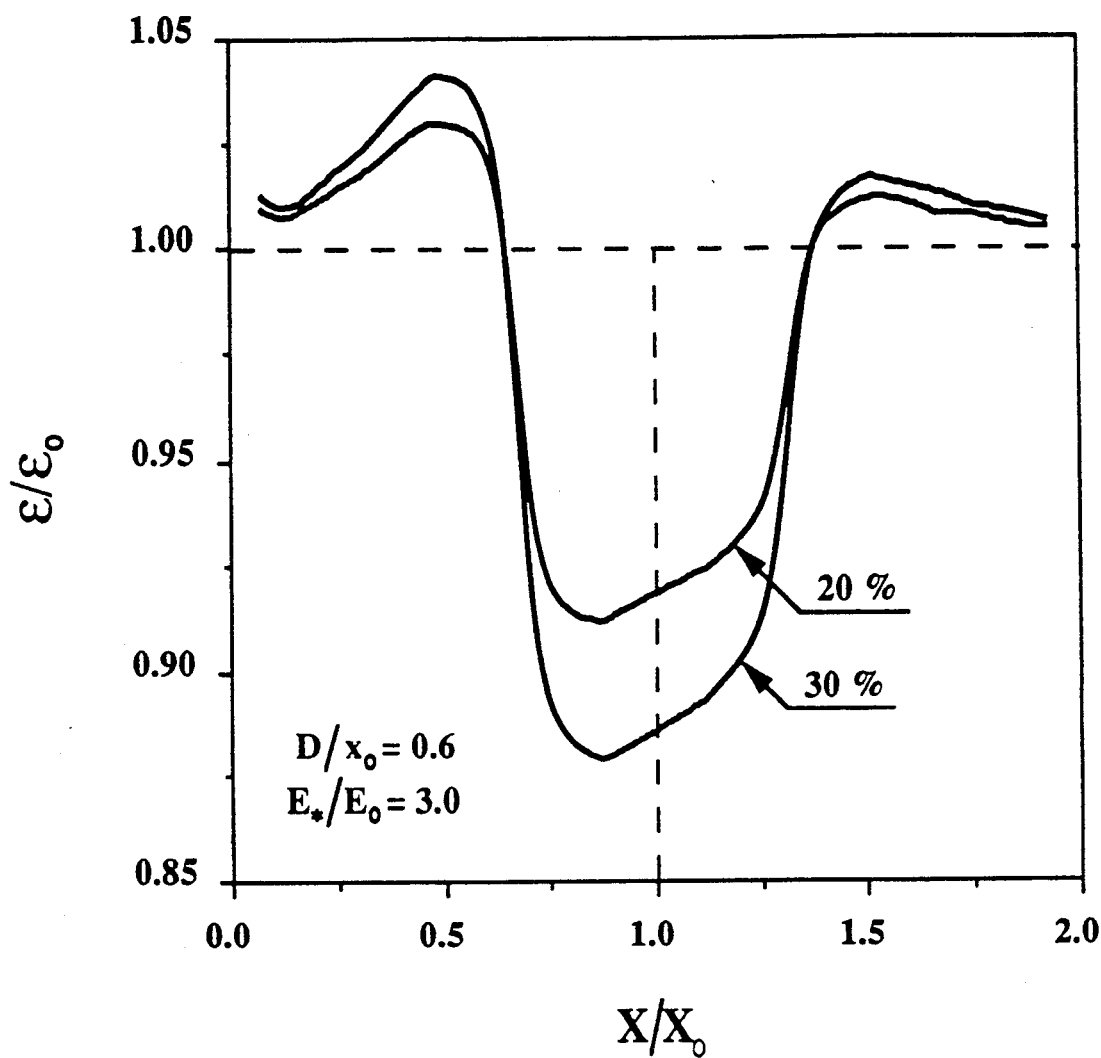

The size of a tumor also can be detected in the same manner as is presented in the curves plotted in FIG. 7. The profiles $\epsilon/\epsilon_0$ for two different diameters (e.g. $D/x_0 = 0.4$ and $D/x_0 = 0.6$) of the tumor are shown. The location ($x_0$) of the center of the tumor is the same in both cases and the relative value $E*/E_0$ of the Young's moduli identified in FIG. 3 is listed in the lower left hand corner of FIG. 7.

The curves plotted in FIGS. 4-7 are calculated in the case where the pressure on the interior of the sheath provides 20% deformation of the interior conduit wall surface. The effects shown in FIGS. 4-7 can be enhanced by the increasing of the interior pressure of the sheath, and therefore, the effect of the amount of deformation of the bodily conduit wall is shown in the curves in FIG. 8 for two different values (20% and 30%) of deformation of the interior wall surface of the bodily conduit.

The diagnostic analysis illustrated in FIGS. 4-8 is applicable for analyzing tumors located inside the wall tissue 100 in FIG. 3 as well as inside the prostate 102.

Therefore, the tumor, which can be considered to be a hard or inelastic tumor (or in some cases softer than surrounding tissue), will respond to deformation differently from the surrounding tissue and can be fully quantitatively analyzed.

After imaging as desired at one longitudinal position of the conduit 10, the probe 16 can be slid to a new longitudinal position, where a new set of images may then be taken. The cross sectional images can be taken very rapidly when a phased array ultrasonic transducer 18 is used. Using this set of images, three dimensional reconstruction of internal structures of interest, e.g., tumor, can be made. The tumor may be in a gland or organ 45 adjacent to the conduit and the deformation caused will aid in diagnosis. For example, the prostate can be examined with a transrectal or endorectal probe and the variations in pressure of the sheath will cause different deformations in the prostate.

The probe deforms adjacent tissue and organs as well, for example as mentioned above, an endorectal probe will be capable of deforming the prostate for analysis of any tumor located in the prostate. An esophagal probe permits deforming of the tissue of the throat and larynx for analysis. An endovaginal probe permits deforming tissue and any tumors in the vaginal area (e.g., cervix). The deformation, as explained above, permits evaluating the "hardness" or elasticity of internal tissue by characterizing tissues seen on an ultrasonic image in terms of elasticity, quantitatively expressed as Young $\propto$ s or shear moduli.

The present invention permits obtaining quantitative and objective palpatory information about tumors adjacent a bodily conduit in a manner far exceeding the subjective intracavity finger palpation method. The present invention allows one to reliably obtain information about the presence, location, size, and relative hardness of a tumor whereas the conventional finger palpation method is only marginally successful in detecting the presence of tumors much less determining the size, precise location, and relative hardness of a tumor. The present invention is particularly advantageous in detecting and objectively assessing tumors that would be too small or too far away from the bodily conduit wall to be detected by conventional finger palpation methods.

The probe of the present invention provides a way of obtaining different deformation of tissue using an endocavity probe that has an expandable sheath which can be expanded using a controlled source of pressure to deform the cavity or bodily conduit and adjacent tissue, at least in a localized area overlying a transducer that permits imaging of tissues. The tissue is imaged before it is compressed by expanding the sheath, and after a desired expansion of the sheath to cause a desired percentage of compression of the tissue, the tissue is again imaged. Successive readings of greater deformation of the tissue can be taken to provide data for calculating the elasticity of tissue in the regions of interest. The elasticity is an informative characteristic for detection of tumors, for example, cancerous tumors in various parts of the body.

Although the present invention has been described with reference to preferred embodiments, workers skilled in the art will recognize that changes may be made in form and detail without departing from the spirit and scope of the invention.

WHAT IS CLAIMED IS:

1. An device for palpating tissue comprising:
   an extra candy probe an imaging transducer adjacent one end thereof;
   said probe being of size to fit in within a bodily conduit to examined;
   an outer sheath of expandable elastic material placed over the transducer and an end of the, probe to be inserted in the bodily conduit;
   means for providing an internal fluid under pressure within the sheath between the probe and an inner surface of the sheath to provide expansion of the sheath to at least partially engage the interior surface of the bodily conduit and compress a conduit wall and tissue adjacent to the conduit wall; and
   control means for operating the transducer at selected times correlated to the application of compression to the tissue for determining elasticity characteristics of tissue being imaged by the transducer.

2. The device as specified in claim 1, comprising pressure control means for controlling the pressure of the fluid on the interior of the sheath to at least two separate pressures.

3. The device of claim 1 wherein said sheath has a portion in a region adjacent to the transducer and the probe that is less resistant to expansion under fluid pressure to cause increased deformation of tissue in such region.

4. A method of quantitatively obtaining palpation information of tissue surrounding a bodily conduit, said conduit having a wall made of tissue and being within surrounding tissue comprising the steps of:
   inserting a probe assembly into the bodily conduit, said probe assembly including a transducer for imaging bodily tissue;
   providing an outer sheath over the probe that is flexible and capable of being expanded to engage the wall of the bodily conduit and cause compression of such wall and tissue surrounding the walls;
   introducing a fluid under pressure on the interior of the flexible sheath to expand the sheath and compress tissue in at least localized areas contacted by the probe; and
   obtaining images of tissue that correlate to the elasticity of the tissue before deforming the tissue, and subsequent to deforming the tissue.

5. The method claim 4 wherein the obtaining of the images is accomplished with moving the probe along the bodily conduit and making a three-dimensional reconstruction of the imaged tissue under different compression loadings, and calculating elastic moduli of tissues.

6. The method of claim 4 including the step of altering the compression in a selected sequence of steps and obtaining images at each successive step for analyzing the elasticity of tissue being imaged.

* * * * *

UNITED STATES PATENT AND TRADEMARK OFFICE
CERTIFICATE OF CORRECTION

PATENT NO. : 5,265,612
DATED : November 30, 1993
INVENTOR(S) : Armen P. Sarvazyan et al.

It is certified that error appears in the above-indentified patent and that said Letters Patent is hereby corrected as shown below:

Column 7, Line 25, (Claim 1, Line 1), cancel "An" and insert --A--;

Line 26, cancel "extra candy probe" and insert --intracavity probe,--.

Signed and Sealed this

Seventh Day of June, 1994

*Attest:*

BRUCE LEHMAN

*Attesting Officer*     *Commissioner of Patents and Trademarks*